(12) United States Patent
Redei (10) Patent No.: US 6,372,713 B1
(45) Date of Patent: Apr. 16, 2002

(54) ANTI-DEPRESSANT EFFECTS OF CORTICOTROPIN RELEASE INHIBITING FACTOR

(75) Inventor: Eva Redei, Chicago, IL (US)

(73) Assignee: The Board of Trustees of Northwestern University, Evanston, IL (US)

( * ) Notice: Subject to any disclaimer, the term of this patent is extended or adjusted under 35 U.S.C. 154(b) by 0 days.

(21) Appl. No.: 09/366,981

(22) Filed: Aug. 4, 1999

Related U.S. Application Data (63) Continuation-in-part of application No. 08/660,561, filed on Jun. 7, 1996, now Pat. No. 6,039,956, which is a continuation-in-part of application No. 08/523,125, filed on Sep. 8, 1995, now Pat. No. 5,830,866.
(60) Provisional application No. 60/140,962, filed on Jun. 24, 1999.

(51) Int. Cl.[7] .................................................. A61K 38/00
(52) U.S. Cl. ....................................................... 514/2
(58) Field of Search .............................. 514/12, 18, 13, 514/2; 530/326–331, 306; 930/10, 70

(56) References Cited

U.S. PATENT DOCUMENTS

| | | | |
|---|---|---|---|
| 4,160,452 A | 7/1979 | Theeuwes | 128/260 |
| 4,256,108 A | 3/1981 | Theeuwes | 128/260 |
| 4,265,874 A | 5/1981 | Bonsen et al. | 424/15 |
| 5,334,702 A | 8/1994 | Greene et al. | 530/323 |
| 5,830,866 A | 11/1998 | Redei et al. | 514/18 |
| 6,039,956 A | * 3/2000 | Redei et al. | 424/198.1 |

FOREIGN PATENT DOCUMENTS

WO    WO 96/08265    * 3/1996

OTHER PUBLICATIONS

L. Stryer. Biochemistry, 3rd Edition, W.H. Freeman and Co., New York, pp. 794–795 (1988).*
Bingaman et al., 1993, Neuroendocrinology 59:228–234.
Hanada et al., 1997, Neurosci. Abst. 23:119.
McGivern et al., 1997, J. Neurosci. 17:4886–4894.
Pare and Redei, 1993, J. Physiol. 87:229–238.
Redei et al., 1995, Endocrinology 136:3557–3563.
Redei et al., 1995, Endocrinology 136:1813–1816.

* cited by examiner

*Primary Examiner*—John S. Brusca
(74) *Attorney, Agent, or Firm*—Morgan, Lewis & Bockius, LLP (57) ABSTRACT

Methods and compositions for treatment of depression in animals are provided.

15 Claims, 5 Drawing Sheets

SEQUENCE LISTING

<160> NUMBER OF SEQ ID NOS: 5

<210> SEQ ID NO 1
<211> LENGTH: 22
<212> TYPE: PRT
<213> ORGANISM: Rattus sp.

<400> SEQUENCE: 1

Phe Ile Asp Pro Glu Leu Gln Arg Ser Trp Glu Glu Lys Glu Gly Glu
 1               5                  10                  15

```
Gly Val Leu Met Pro Glu
            20

<210> SEQ ID NO 2
<211> LENGTH: 23
<212> TYPE: PRT
<213> ORGANISM: Mus sp.

<400> SEQUENCE: 2

Phe Ile Asp Pro Glu Leu Gln Arg Ser Trp Glu Glu Thr Glu Gly Glu
 1               5                  10                  15

Glu Gly Gly Leu Met Pro Glu
            20

<210> SEQ ID NO 3
<211> LENGTH: 9
<212> TYPE: PRT
<213> ORGANISM: Rattus sp.

<400> SEQUENCE: 3

Glu Gly Glu Gly Val Leu Met Pro Glu
 1               5

<210> SEQ ID NO 4
<211> LENGTH: 4
<212> TYPE: PRT
<213> ORGANISM: Rattus sp.

<400> SEQUENCE: 4

Leu Met Pro Glu
 1

<210> SEQ ID NO 5
<211> LENGTH: 26
<212> TYPE: PRT
<213> ORGANISM: Homo sapiens

<400> SEQUENCE: 5

Leu Ala Asp Pro Lys Ala Gln Arg Ser Trp Glu Glu Glu Glu Glu Glu
 1               5                  10                  15

Glu Glu Arg Glu Glu Asp Leu Met Pro Glu
            20                  25
```

ANTI-DEPRESSANT EFFECTS OF CORTICOTROPIN RELEASE INHIBITING FACTOR

CROSS REFERENCE TO RELATED APPLICATIONS

This application is a continuation-in-part of U.S. application Ser. No. 08/660,561, filed on Jun. 7, 1996, now U.S. Pat. No. 6,039,956, issued on Mar. 21, 2000, and ultimately claims priority of U.S. application Ser. No. 08/523,125, filed on Sep. 8, 1995. Co-pendency between the present application and U.S. application Ser. No. 08/523,125 is established as follows: The present application claims priority under 35 U.S.C. §119(e) to U.S. Provisional Application No. 60/140, 962, filed on Jun. 24, 1999, which was co-pending with U.S. application Ser. No. 08/660,561 filed on Jun. 7, 1996, now U.S. Pat. No. 6,039,956 issued on Mar. 21, 2000. U.S. application Ser. No. 08/660,561 is a continuation-in-part of U.S. application Ser. No. 08/523,125, filed on Sep. 8, 1995, now U.S. Pat. No. 5,830,866, issued on Nov. 3, 1998.

BACKGROUND OF THE INVENTION

Stressful life events are thought to precipitate depressive episodes in vulnerable individuals. There appears to be a biochemical link between stress and depression since dysregulation of the stress-responsive hypothalamic-pituitary-adrenal (HPA) axis, manifested in cortisol hypersecretion, frequently occurs in melancholic depressed patients, and remission from depression leads to normalization of this dysregulation. Inversely, decreasing the levels and efficacy of glucocorticoids can ameliorate symptoms of depression. Thus, there is clinical evidence that hypercortisolemia may be associated with the pathophysiology of a subtype of depression.

Synthesis and secretion of glucocorticoids is regulated by ACTH which in turn is primarily stimulated by the hypothalamic corticotropin releasing factor (CRF). CRF appears to mediate not only the endocrine, but also the autonomic and behavioral responses to stress, the later event occurring directly in the brain. Increased production of CRF is thought to be involved in the etiology of depression. Thus, CRF receptor antagonists have been developed and tested for their anxiolytic and antidepressant characteristics.

Recently studies demonstrated that prepro-TRH 178-199, a peptide derived from the TRH precursor, inhibits ACTH secretion in vitro (Redei et al., 1995, Endocrinology 136:1813–1816; Redei et al., 1995, Endocrinology 136:3557–3563) and plasma ACTH, CORT, and prolactin responses to stressors in vivo (McGivern et al., 1997, J. Neurosci. 17:4886–4894). It has also been reported that centrally administered prepro-TRH 178-199 produced behavioral effects in rats in paradigms used to assess response to novelty and anxiolytic potential (McGivern et al., 1997, J. Neurosci. 17:4886–4894). Intracerebroventricular (i.c.v.) administration of prepro-TRH 178-199 into the lateral ventricle induced significant increases of locomotion in the open field test of time spent in the open arms of the elevated plus maze and in the light compartment of the light/dark box. Thus, prepro-TRH 178-199, administered directly into the brain, increases arousal and exploratory behavior, and decreases anxiety in experimental paradigms routinely used to assess these behaviors in animals.

Currently, while anti-depressive therapeutic compounds are available, each of these compounds may have deleterious side effects. There is therefore a need in the art for the discovery and development of additional compounds which alleviate depression. The present invention satisfies this need.

SUMMARY OF THE INVENTION

The invention relates to a method of treating a depressive disorder in an animal. The method comprises administering to said animal a compound having CRIF biological activity.

In one aspect, the compound is a peptide.

In another aspect, the compound is a peptidometic.

In yet another aspect, the compound is in a therapeutically effective amount.

In a further aspect, the compound is in a pharmaceutically acceptable carrier.

In yet another aspect, the animal is a human.

In another aspect, the compound is administered to the animal by a route selected from the group consisting of oral, parenteral, intranasal and central.

In one embodiment, the peptide is a CRIF peptide comprising at least three amino acids positioned between the fourth and fifth TRH peptide on a prepro-TRH molecule.

In a further embodiment, the CRIF peptide comprises from three to twenty two amino acids positioned between the fourth and fifth TRH peptide on a prepro-TRH molecule.

In another embodiment, the CRIF peptide comprises the sequence Phe-Ile-Asp-Pro-Glu-Leu-Gln-Arg-Ser-Trp-Glu-Glu-Lys-Glu-Gly-Glu-Gly-Val-Leu-Met-Pro-Glu (SEQ ID NO:1).

In yet another embodiment, the CRIF peptide comprises the sequence Phe-Ile-Asp-Pro-Glu-Leu-Gln-Arg-Ser-Trp-Glu-Glu-Thr-Glu-Gly-Glu-Glu-Gly-Gly-Leu-Met-Pro-Glu (SEQ ID NO:2).

In another embodiment, the CRIF peptide comprises the sequence Glu-Gly-Glu-Gly-Val-Leu-Met-Pro-Glu (SEQ ID NO:3).

In a further embodiment, the CRIF peptide comprises the sequence Leu-Met-Pro-Glu (SEQ ID NO:4).

In yet another embodiment, the CRIF peptide comprises from three to twenty six amino acids positioned between the fourth and fifth TRH peptide on a prepro-TRH molecule.

In another embodiment, the CRIF peptide comprises the sequence Leu-Ala-Asp-Pro Lys-Ala-Gln-Arg-Ser-Trp-Glu-Glu-Glu-Glu-Glu-Glu-Glu-Arg-Glu-Glu-Asp-Leu-Met-Pro-Glu (SEQ ID NO:5).

In a further aspect, the depressive disorder is selected from the group consisting of major depression, minor depression, bipolar disorders, disthymia, cyclothymia, and premenstrual syndrome.

BRIEF DESCRIPTION OF THE DRAWINGS

Magnification using a 20× objective.

DETAILED DESCRIPTION OF THE INVENTION

The invention relates to the discovery that administration of prepro-TRH 178-199, or peptides derived therefrom, to the brain of an animal exhibiting depressed behavior alleviates the depression.

Prepro-TRH 178-199 is also know herein as corticotropin release inhibiting factor (CRIF). As the data provided herein establish, CRIF peptides having various lengths are useful in the methods of the invention. Essentially, the data establish that central sub-acute administration of CRIF dose-responsively inhibits immobility of rats in a forced swim test, a standard test of antidepressant drug efficacy. The data further illustrate that the anti-depressant activity of CRIF is not limited to the particular animal being tested, in that, it is evident that two different strains of rats respond to CRIF. In addition, the data establish that chronic administration of CRIF to the rats results in more pronounced anti-depressant activity compared with sub-acute administration of CRIF. Further, peptides derived from the C-terminus of CRIF are equally capable of alleviating depression in the rats.

The invention therefore includes a method of treating a depressive disorder in an animal, comprising administering CRIF, or peptides derived therefrom, to the animal. Preferably, the animal is a human.

The term "depressive disorder" as used herein, should be construed to include major depression, minor depression, bipolar disorders, disthymia, cyclothymia, and premenstrual syndrome. The term should be specifically construed to exclude anxiety in the absence of depressive symptoms.

The isolation and characterization of CRIF peptide is disclosed in U.S. Pat. No. 5,830,866 (which is hereby incorporated herein by reference in its entirety). Peptides having CRIF activity are those which comprise at least three contiguous amino acids contained within the amino acid sequence positioned between the fourth and fifth thyrotropin releasing hormone sequence on a prepro-thyrotropin releasing hormone protein. Full-length CRIF is designated herein as rat prepro-TRH 178-199, which identifies CRIF as being amino acid numbers 178-199 on the rat prepro-TRH molecule. However, the invention should in no way be construed as being limited to full-length CRIF. Rather, as the data presented herein establish, peptides which have fewer amino acids than full length CRIF, have CRIF biological activity, as that term is defined herein. For example, peptides having as few as four amino acids and peptides having at least nine amino acids positioned within the prepro-TRH 178-199 molecule have CRIF biological activity according to the results of experiments presented herein.

Full length rat CRIF peptide comprises twenty two contiguous amino acids in length, wherein CRIF is located between the fourth and fifth TRH in the prepro-TRH molecule. Thus, full length rat CRIF is also known as prepro-TRH-178-199. Full length human CRIF comprises twenty six contiguous amino acids in length, wherein CRIF is located between the fourth and fifth TRH in the human prepro-TRH molecule. Full length human CRIF is also known as human prepro-TRH 158-183.

The invention should be construed to include any and all CRIF peptides comprising amino acid lengths which range from at least three contiguous amino acids to as much as twenty two amino acids in length, being positioned within the rat prepro-TRH 178-199 molecule. The CRIF peptide of the invention may therefore comprise at least three contiguous amino acids in length, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, and up to twenty two contiguous amino acids in length, wherein the peptide is positioned within the rat prepro-TRH 178-199 molecule. Preferably, the CRIF peptide of the invention comprises either four or nine amino acids in length. Preferred rodent CRIF sequences include from three to twenty two contiguous amino acid sequences of the sequence Phe-Ile-Asp-Pro-Glu-Leu-Gln-Arg-Ser-Trp-Glu-Glu-Lys-Glu-Gly-Glu-Gly-Val-Leu-Met-Pro-Glu (SEQ ID NO:1) (full length rat CRIF) and the sequence Phe-Ile-Asp-Pro-Glu-Leu-Gln-Arg-Ser-Trp-Glu-Glu-Thr-Glu-Gly-Glu-Glu-Gly-Gly-Leu-Met-Pro-Glu (SEQ ID NO:2) (full length mouse CRIF), and also the sequence Glu-Gly-Glu-Gly-Val-Leu-Met-Pro-Glu (SEQ ID NO:3) (a rat CRIF peptide), the sequence Leu-Met-Pro-Glu (SEQ ID NO:4) (another rat CRIF peptide), and any derivatives and analogs thereof which retain the biological activity of CRIF as defined herein.

Most preferably, the CRIF peptide of the invention is from three to twenty two contiguous amino acids positioned within the prepro-TRH 178-199 molecule.

With respect to human CRIF, full length human CRIF comprises twenty six contiguous amino acids in length, wherein CRIF is located between the fourth and fifth TRH in the human prepro-TRH molecule. The invention should therefore be construed to include any and all human or other higher mammalian CRIF peptides comprising amino acid lengths which range from at least three contiguous amino acids to as much as twenty six amino acids in length, being positioned within the human prepro-TRH 158-183 molecule. The CRIF peptide of the invention may therefore comprise at least three contiguous amino acids in length, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four, at least twenty five, and up to twenty six contiguous amino acids in length, wherein the peptide is positioned within the human prepro-TRH 158-183 molecule.

A preferred human CRIF is a peptide having from three to twenty six contiguous amino acids of the sequence Leu-Ala-Asp-Pro Lys-Ala-Gln-Arg-Ser-Trp-Glu-Glu-Glu-Glu-Glu-Glu-Glu-Glu-Arg-Glu-Glu-Asp-Leu-Met-Pro-Glu (SEQ ID NO:5) (full length human CRIF).

The present invention also provides for the use of analogs of peptides having CRIF activity. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;

valine, isoleucine, leucine;

aspartic acid, glutamic acid;

asparagine, glutamine;

serine, threonine;

lysine, arginine; and phenylalanine, tyrosine.

Other modifications, which do not normally alter the primary sequence but which may be useful, include in vivo or in vitro chemical derivatization of peptides, e.g., amidation, acetylation, or carboxylation, and modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are peptides which have phosphorylated amino acid residues, e.g., phosphotyrosine, phosphoserine, or phosphothreonine.

Also included are peptides which have been modified using ordinary molecular biological techniques so as to improve their resistance to proteolytic degradation or to optimize solubility properties or to render them more suitable as a therapeutic agent. Analogs of such peptides include those containing residues other than naturally occurring L-amino acids, e.g., D-amino acids or non-naturally occurring synthetic amino acids. The peptides of the invention are not limited to products of any of the specific exemplary processes listed herein.

It will thus be appreciated that the peptides may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound as an anti-inflammatory agent, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$–$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitice, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in therapeutic settings.

CRIF-like peptides and CRIF may also be used for the generation of peptidometics and other small molecules useful for treatment of such disorders. Peptidomimetics may be generated using techniques described in PCT/US93/01201 and in U.S. Pat. No. 5,334,702.

Thus, the invention should also be construed to include a method of treating a depressive disorder comprising administering a CRIF peptidometic to the animal.

In the methods of the invention, the CRIF peptide (or any analog, or peptidometic derived therefrom) is administered to the animal so as to be delivered to the brain of the animal for alleviation of depressive disorder in the animal. Suitable routes of administration therefore include oral, parenteral, intranasal and intrathecal (central). The smaller the CRIF peptide, the more likely that it will cross the blood brain barrier when administered using a route other than direct brain administration and therefore enter the brain tissue wherein the effects of the peptide are manifested.

CRIF peptides which are useful in the methods of the invention may be formulated and administered to an animal for treatment of a depressive disorder are now described.

The invention encompasses the preparation and use of pharmaceutical compositions comprising a CRIF peptide useful for treatment of a depressive disorder as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats and dogs.

Pharmaceutical compositions that are useful in the methods of the invention may be prepared, packaged, or sold in formulations suitable for oral, parenteral, intranasal, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para- hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Pharmaceutical compositions of the invention formulated for intranasal delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

Formulations suitable for central administration include saline salts and the addition of other ingredients which render the compound more stable in the brain.

Typically dosages of the compound of the invention which may be administered to an animal, preferably a human, range in amount from 1 μg to about 100 g per killogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per killogram of body weight of the animal. More preferably, the dosage will vary from about 10 mg to about 1 g per killogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

Definitions

The articles "a" and "an" are used herein to refer to one or to more than one (i.e. to at least one) of the grammatical object of the article. By way of example, "an element" means one element or more than one element.

As used herein, "alleviating a depressive disorder" means reducing the severity of at least one symptom associated with the depressive disorder. The term "alleviating" is used synonymously herein with the term "treating."

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

Depression in an animal is "alleviated" if the severity of a symptom of the depression, the frequency with which such a symptom is experienced by an animal, or both, are reduced.

"Depression" as used herein refers to major depression, minor depression, bipolar disorders, disthymia, cyclodisthymia, and premenstrual syndrome. It is used herein synonymously with the term "depressive disorder." The term should be specifically construed to exclude anxiety.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"CRIF-like activity" as used here denotes an activity which is so similar to that of CRIF, i.e., which functions by the same mechanism as CRIF, so as to be virtually indistinguishable from CRIF. However, this term as used herein, should also be construed to encompass compounds which may operate by the same mechanism as CRIF, but which may have a higher specific activity than CRIF.

By the term "CRIF-related disorder" as used herein is meant any disease or disorder in an animal which can be alleviated, prevented or otherwise treated by manipulating CRIF in the animal.

"Peripheral administration" as used herein, denotes administration of a compound to an animal by any route other than direct administration to the brain. Thus, peripheral administration includes, but is not limited to, oral, nasopharyngeal, intraperitoneal, intramuscular and intravenous administration of any of the compounds of the invention.

"Central administration" as used herein, denotes administration of a compound directly to the brain. This term is used herein synonymously with the term "intrathecal administration."

A "therapeutic" treatment is a treatment administered to an animal, including a human, which exhibits signs of pathology for the purpose of diminishing or eliminating those signs.

A "therapeutically effective amount" of a compound is that amount of compound which is sufficient to provide a beneficial effect to the animal to which the compound is administered.

The invention is now described with reference to the following examples. These examples are provided for the purpose of illustration only and the invention should in no way be construed as being limited to these examples but rather should be construed to encompass any and all variations which become evident as a result of the teaching provided herein.

EXAMPLE 1

Antidepressant-like Properties of Prepro-TRH 178-199: Acute Effects in the Forced Swim Test The experiments presented in this example may be summarized as follows.

The data disclosed herein demonstrate the effects of a neuropeptide, rat prepro-TRH 178-199, on the Porsolt forced swim test (FST) of depression in rats. Sub-acute intracerebroventricular (i.c.v.) administration of prepro-TRH 178-199 significantly and dose-responsively reduced floating and increased active behavior in the FST. Chronic (14 days) administration of 6 $\mu$g/kg prepro-TRH 178-199 decreased floating and increased climbing significantly with no significant differences between chronic and sub-acute treatment effects on active behavior.

The data disclosed herein further demonstrated that the biological activity of this peptide resides in the C-terminal fragment as prepro-TRH 178-199 and prepro-TRH 191-199 exhibited equally potent anti-depressant activity in the FST. These data suggest that the bioactive neuropeptide prepro-TRH 178-199 has antidepressant-like activity, and therefore, that endogenous prepro-TRH 178-199 contributes to the etiology or manifestation of depressive behavior.

The Materials and Methods used in the experiments presented in this example are now described.

Animals

Adult male Sprague-Dawley or F1 Brown Norway/Fisher344 rats were used in these experiments presented herein. The rats were implanted with cannulae into the lateral ventricle as described previously (McGivern, 1997, J. Neurosci. 17:4886–4894). For purposes of the stereotaxic surgery, the animals were anesthetized (ketamine, 50 mg/kg/xylazine, 8 mg/kg) and were positioned in a stereotaxic head frame. At the end of behavioral testing, placements were verified by anesthetizing the animal with pentobarbital (45 mg/kg) and injecting 1 $\mu$l Trypan Blue staining solution through the cannulae just prior to decapitation. Only data from animals with confirmed correct cannulae placement were included in the analysis.

At least 7 days after the stereotaxic surgery, the animals were subjected to an initial 15 minute swim pretest, followed by a 5 minute swim test 24 hours later. The rats received two injections of sterile vehicle (1.5, 3.0, 6.0 or 12.0 $\mu$g/kg) or prepro-TRH 178-199 (0.6, 1.2., 2.3 and 4.6 nmol/kg) in a 2–3 $\mu$l volume between the pretest and the test: 15 minutes after the initial (pre)-swim and 5 minutes before the test swim. In the case of prepro-TRH 191-199 administration, the C-terminal peptide was administered in this sub-acute fashion at 2.2 $\mu$g/kg (2.3 nmol/kg) dose, which is equivalent to 6 $\mu$g/kg prepro-TRH 178-199.

In the chronic treatment experiment, 6 $\mu$g/kg prepro-TRH 178-199 or sterile water vehicle was injected i.c.v. daily for 13 days. On the fourteenth day, a forced swim 15 minutes pretest was carried out followed by injection of prepro-TRH 178-199 or vehicle 15 minutes later. Twenty hours later, the animals received an i.c.v. injection of prepro-TRH 178-199 or an injection of vehicle and 5 minutes later they were tested in the 5 minute swim test.

Forced swim test (FST)

The forced swim test (FST) utilized a glass water tank 30 cm in diameter and 45 cm tall with the water level 15 cm from the top and the water temperature set at 25° C. The rats were individually placed in the water tank for 15 minutes. Twenty-four hours later, the rats were placed once more in the tank for a 5 minute session and the tests were videotaped. The videotapes were scored by a trained observer who was blind to the treatment conditions and the time spent floating, and time spent swimming and climbing were recorded.

The Results of the experiments presented in this example are now described.

Figure 1:
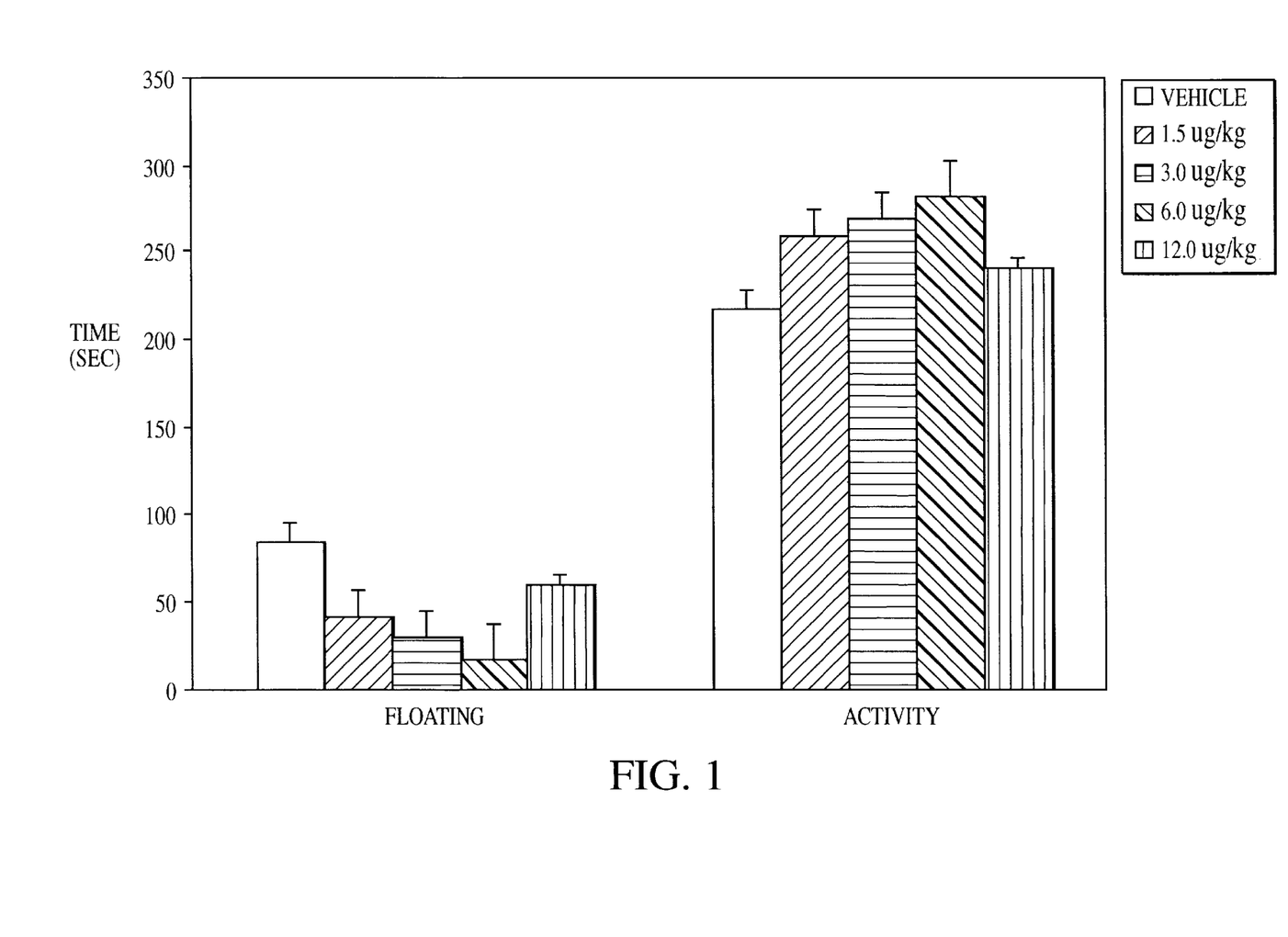
FIG. 1 is a graph depicting the effects of centrally administered prepro-TRH 178-199 on floating and activity in the forced swim test. Rats were treated with vehicle or prepro-TRH 178-199 (1.5, 3.0, 6.0, 12.0 μg/kg body weight) 15 minutes after the first 15 minute swim and 5 minutes before the second 5 minute swim. Floating time is measured when the animals are immobile and activity included swimming and climbing behaviors. Each value represents the mean±SEM of 6 (vehicle) or 7 (peptide) rats.

Sub-acute i.c.v. administration of various doses of prepro-TRH 178-199 to male Sprague-Dawley rats had a significant effect on floating behavior (F[4,29]=5.04, p=0.004, FIG. 1). The 1.5, 3.0 and 6.0 $\mu$g/kg doses significantly (p<0.05, respectively) reduced the floating time, while the 12.0 $\mu$g/kg dose had no effect, resulting in a bell-shape dose-response curve. The time spent with active behavior was also significantly increased by prepro-TRH 178-199 (F[4,32]=3.27; p=0.025, FIG. 1). This increased activity reached significance (p<0.05) at the 3 and 6 $\mu$g/kg doses. When activity is divided into climbing and swimming, there were no significant differences between the treatment groups.

Figure 2:
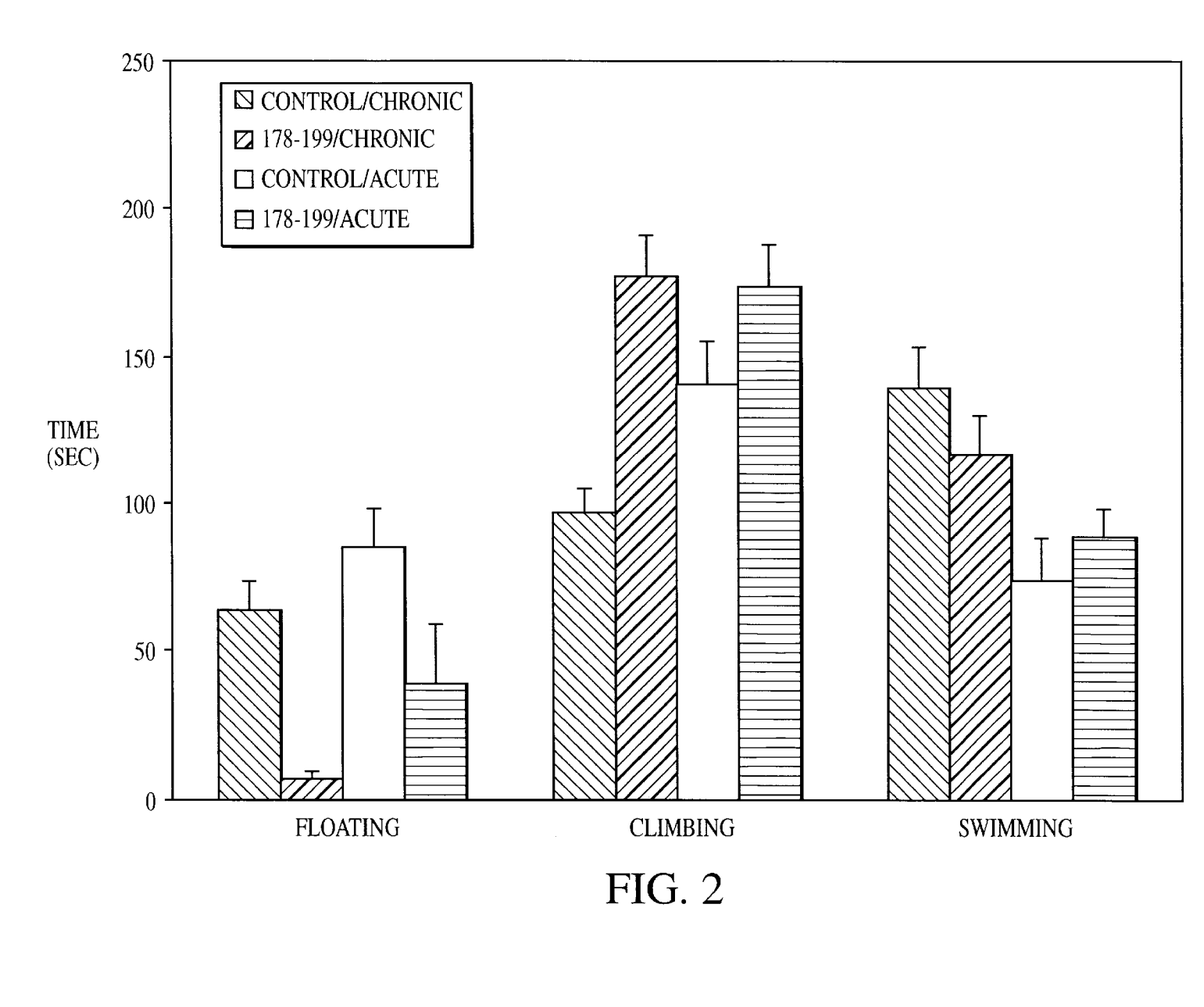
FIG. 2 is a graph depicting the effects of central sub-acute and chronic administration of prepro-TRH 178-199 on floating, climbing and swimming in the forced swim test. Rats were treated with vehicle or 6 μg/kg prepro-TRH 178-199 sub-acutely or in a sub-acute manner but after 13 days of daily administration of the same dose of prepro-TRH 178-199. Each value represents the mean±SEM of 7 (chronic vehicle), 10 (chronic peptide), 5 (acute vehicle), 6 (acute peptide) rats.

The effect of sub-acute and chronic administration of 6 $\mu$g/kg prepro-TRH 178-199 on FST behaviors differed only by the potency of the effect (FIG. 2). Chronic administration consisted of daily administration of the peptide or vehicle into the lateral ventricle of adult male Sprague-Dawley rats, while sub-acute administration was essentially a repeat of the dose-response experiment (FIG. 1) at the 6 $\mu$g/kg dose. Floating time was decreased by the administration of the peptide regardless of the length of treatment (F[1,23]=32.4; p<0.001), but chronic administration decreased floating significantly more than did the acute treatment (F[1,23]=8.89; p=0.007, FIG. 2). Within activity measures, climbing increased significantly in response to i.c.v. administration of prepro-TRH 178-199 (F[1,23]=14.8; p=0.001), but there were no significant differences between chronic and sub-acute treatment effects on climbing. Time spent swimming was not altered by either sub-acute or chronic treatment.

Figure 3:
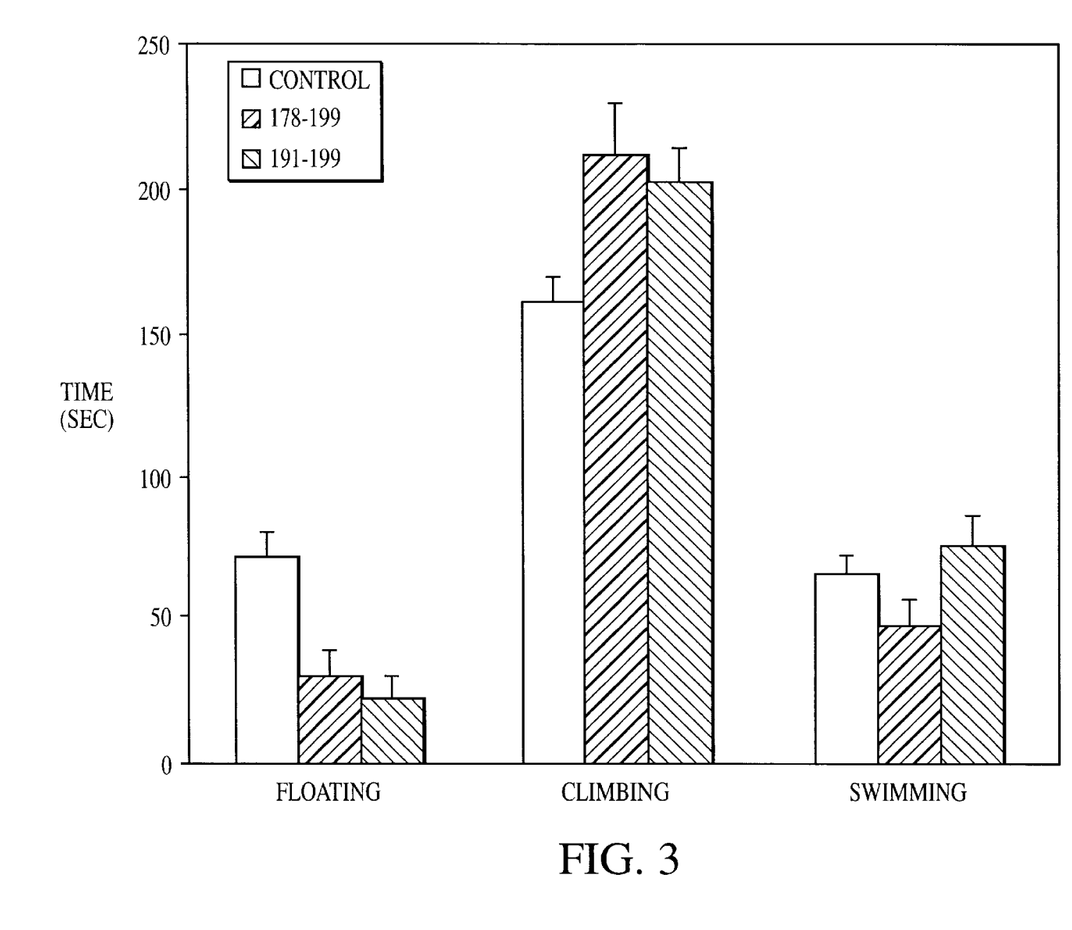
FIG. 3 is a diagram depicting the effects of central sub-acute administration of 6 μg/kg prepro-TRH 178-199 and 2.2 μg/kg prepro-TRH 191-199 on floating, climbing and swimming behavior in the forced swim test. Each value represents the mean+SEM of 7 (vehicle), 8 (prepro-TRH 178-199) and 8 (prepro-TRH 191-199) rats.

In addition, the structure-function relationship of prepro-TRH 178-199 was examined by comparing the effect of the C-terminal fragment (i.e., prepro-TRH 191-199) to that of the full-length peptide using F344XBN rats. Prepro-TRH 191-199 had effects very similar to those of the full-length peptide. Either 2.2 $\mu$g/kg prepro-TRH 191-199 or the equimolar dose of 6 $\mu$g/kg prepro-TRH 178-199 administered in the sub-acute mode, equally and significantly decreased floating (F[2,29]=9.7; p<0.001, FIG. 3) and increased climbing (F[2,29]=6.0; p<0.01), specifically climbing in the FST.

The data disclosed herein examined the antidepressant-like actions of intracerebroventricularly administered prepro-TRH 178-199 by determining its dose-response characteristics in the forced swim test, a standard test of antidepressant drug efficacy. Furthermore, the antidepressant-efficacy of chronic administration of prepro-TRH 178-199 was also determined in the forced-swim test. Finally, the biological activity of the C-terminal fragment, prepro-TRH 191-199, was determined.

The data disclosed herein demonstrate for the first time that i.c.v. administration of prepro-TRH 178-199 decreases immobility in the forced swim test in a dose-dependent fashion. The forced swim test is used for screening antidepressant activity where the potential drug, administered sub-acutely between the pretest and the test sessions, decrease the duration of the behavioral immobility. Therefore, the data disclosed herein indicate the potential antidepressive effect of prepro-TRH 178-199.

EXAMPLE 2

Prepro-TRH 178-199 Immunoreactivity is Altered in the Hypothalamus of the Wistar Kyoto Strain of Rat To further elucidate the involvement of prepro-TRH 178-199 peptide in neuroendocrine as well as behavioral abnormalities, the expression of this peptide in a suggested animal model of depression, the Wistar Kyoto (WKY) strain of rat, was examined in the experiments described herein.

It has been discovered in the present invention that WKY rats (Hanada et al., 1997, Neurosci. Abst. 23:119) that exhibit depressive behavior (Pare and Redei, 1993, J. Physiol. 87:229–238), exhibit a decreased density of fiber staining for prepro-TRH178-199 immunoreactivity in the papastrial nucleus. This brain region is believed to be involved in depressive behavior. This finding supports the idea that CRIF affects depressive behavior.

The experiments presented in this example may be summarized as follows.

Immunohistochemical analysis of prepro-TRH 178-199 in Wistar and WKY rats demonstrated significant strain differences in prepro-TRH 178-199 in the paraventricular nucleus (PVN) of the hypothalamus and in the parastrial nucleus (PSN), but not other brain regions. In the PVN, WKY rats exhibited a significantly lower fiber density ($p<0.002$).

The data disclosed herein suggest that altered levels of prepro-TRH 178-199 in WKY rats results in hyper-activity of the HPA axis and in hyper-emotional behavioral characteristics observed in this rat strain. Such data correlate with prepro-TRH 178-199 involvement in the regulation of the HPA axis and behavior.

The Materials and Methods used in the experiments presented in this example are now described.

Animals

Young adult male Wistar (n=5) and WKY (n=5) rats were anesthetized with sodium pentobarbital (100 mg/kg) and the animals were perfused intracardiacally with 50 ml 0.9% saline followed by 200 ml 4% paraformaldehyde. The flow rate of the paraformaldehyde fixative was maintained at approximately 4 ml/minute. The brains were removed, post-fixed in the same fixative for four hours, and then the brains were cryoprotected with 30% sucrose in 0.025 M PBS. Thirty-six micron thick brain sections were cut frozen on a sliding microtome and the sections were saved in 0.01 M PBS containing 0.1% Na Azide for later immunohistochemical processing.

Immunohistochemistry (IHC)

IHC was performed according to standard procedures (Bingaman et al., 1993, Neuroendocrinology 59:228–234). Briefly, sections were washed three times in 0.01 M PBS with 0.1% Triton-X (TX) for 15 minutes to rinse off the storage buffer. The sections were incubated in 0.3% $H_2O_2$ in 0.01 M PBS/TX for 15 minutes and then rinsed 2× in PBS/TX for one hour at room temperature (RT). The sections were then incubated with a rabbit polyclonal antibody directed against prepro-TRH 178-199 (used at 1:10,000 dilution) overnight at RT. Following subsequent washes (3× in PBS/TX for 10 minutes each), the brain sections were incubated with biotinylated goat anti-rabbit IgG (Vector Laboratories, Inc.; 1,200 dilution) in PBS/TX with 2% NGS for two hours at RT. The sections were washed 3× for 10 minutes in PBS/TX and were processed according to the avidin-biotin-peroxidase procedure (ABC, Vector Laboratories, Burlingame, Calif.). Sections were then washed 2× in PBS for 15 minutes and rinsed in 0.1 M Tris-HCl buffer for 15 minutes. Subsequently, the sections were developed with 3,3'-diaminobenzidine (DAB, 0.5/mg/ml) in Tris buffer containing 0.03% $H_2O_2$ for two minutes. The reaction was stopped by washing the section twice in PBS for 10 minutes. The sections were mounted on Superfrost Plus slides and coverslipped using Permount (Fisher Scientific).

Figure 4A:
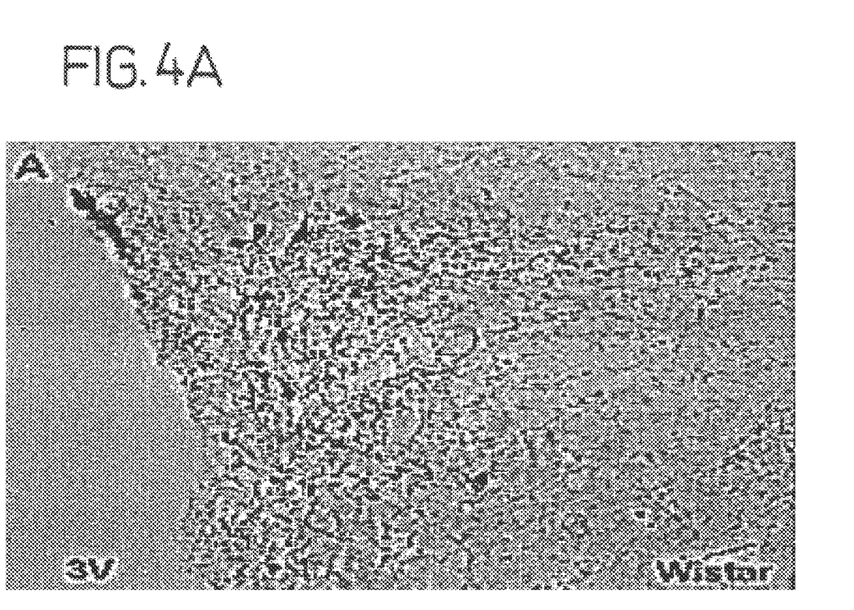
FIG. 4A is an image of a photomicrograph depicting the differential expression of prepro-TRH 178-199 immunoreactivity in Wistar rats. Coronal sections were obtained through the paraventricular nucleus (PVN) of the hypothalmus of the rats. The third ventricle (3V) and the anterior commissure (ac) are indicated. Magnification using a 20× objective.
Figure 4B:
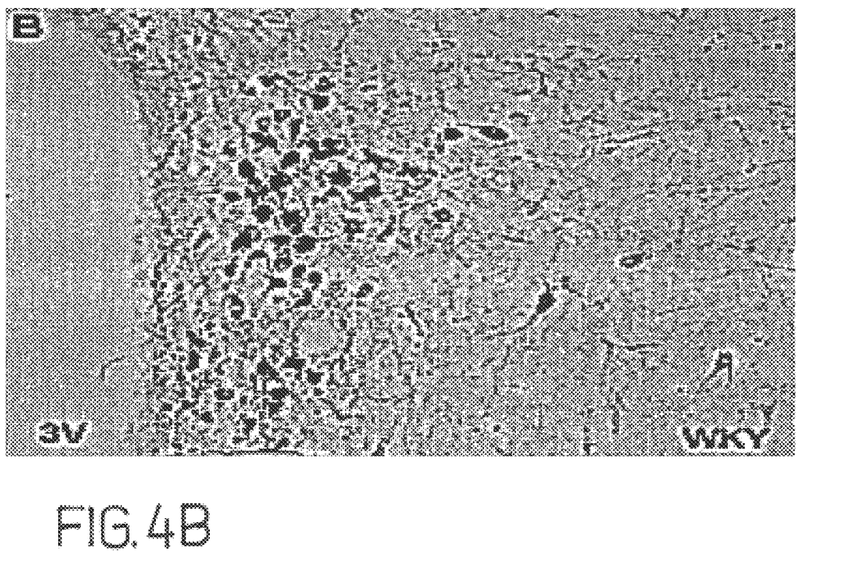
FIG. 4B is an image of a photomicrograph depicting the differential expression of prepro-TRH 178-199 immunoreactivity in WKY rats. Coronal sections were obtained through the paraventricular nucleus (PVN) of the hypothalmus of the rats. The third ventricle (3V) and the anterior commissure (ac) are indicated.
Figure 4C:
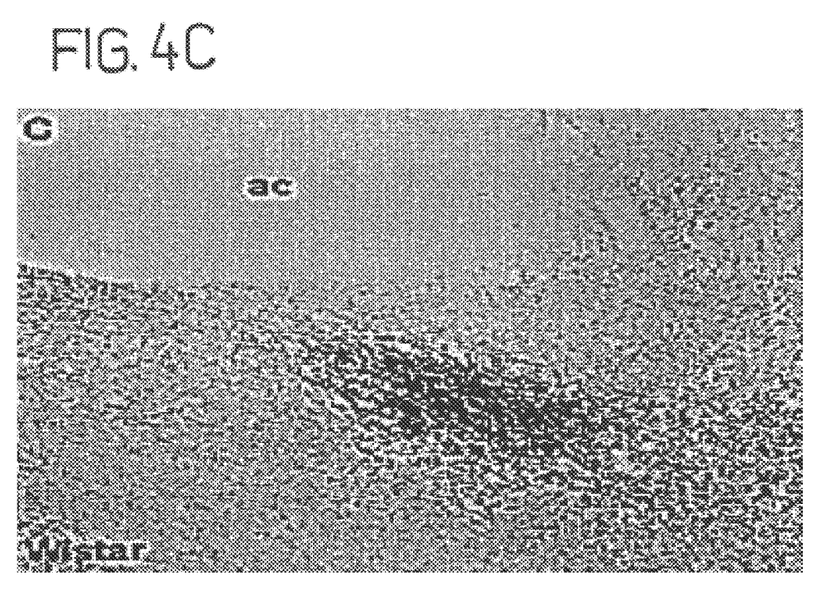
FIG. 4C is an image of a photomicrograph depicting the differential expression of prepro-TRH 178-199 immunoreactivity in Wistar rats. Coronal sections were obtained through the parastrial nucleus (PSN) of the brain of the rats. The third ventricle (3V) and the anterior commissure (ac) are indicated. Magnification using a 20× objective.
Figure 4D:
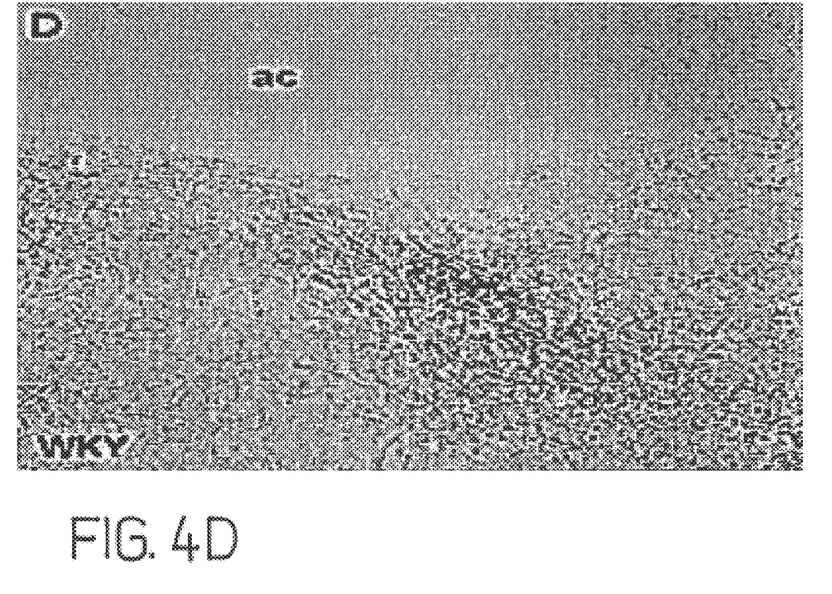
FIG. 4D is an image of a photomicrograph depicting the differential expression of prepro-TRH 178-199 immunoreactivity in WKY rats. Coronal sections were obtained through the parastrial nucleus (PSN) of the brain of the rats. The third ventricle (3V) and the anterior commissure (ac) are indicated. Magnification using a 20× objective.

Immunoreactive (IR) cell profiles and fiber densities were examined in the nucleus accumbens, lateral septum, medial amygdala, dorsomedial nucleus (DMN) of the hypothalamus, paraventricular nucleus (PVN) of the hypothalamus, and the parastrial nucleus (PSN) of Wistar and WKY rats. Among the regions examined, the PVN and the PSN exhibited significant differences in the level of prepro-TRH 178-199 peptide expression between strains. In the PVN, WKY rats had four times the number of IR cell body profiles ($p<0.0005$; FIG. 4A and FIG. 4B) of the Wistar rats. In the same region, however, WKY rats exhibited marginally lower density in nerve fibers when compared to Wistar rats ($p<0.06$; FIG. 4A and FIG. 4B). In the PSN, WKY rats exhibited significantly lower fiber density ($p<0.002$; FIG. 4C and FIG. 4D). The other brain regions examined, including the lateral septum, did not exhibit detectable differences in the expression of prepro-TRH 178-199 peptide between rat strains.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a depressive disorder in an animal, said method comprising administering to said animal a compound comprising Corticotropin Release Inhibiting Factor (CRIF) or having CRIF-like activity, wherein said compound is delivered to the brain of said animal, and further wherein said depressive disorder excludes anxiety.

2. The method of claim 1, wherein said compound is a peptide.

3. The method of claim 2, wherein said peptide is a CRIF peptide comprising at least three contiguous amino acids positioned between the fourth and fifth thyrotropin releasing hormone (TRH) peptide on a prepro-TRH molecule.

4. The method of claim 3, wherein said CRIF peptide comprises from three contiguous to twenty six contiguous amino acids positioned between the fourth and fifth TRH peptide on a prepro-TRH molecule.

5. The method of claim 4, wherein said CRIF peptide comprises the sequence Leu-Ala-Asp-Pro Lys-Ala-Gln-Arg-Ser-Trp-Glu-Glu-Glu-Glu-Glu-Glu-Glu-Glu-Arg-Glu-Glu-Asp-Leu-Met-Pro-Glu (SEQ ID NO:5).

6. The method of claim 3, wherein said CRIF peptide comprises from three contiguous to twenty two contiguous amino acids positioned between the fourth and fifth TRH peptide on a prepro-TRH molecule.

7. The method of claim 6, wherein said CRIF peptide comprises the sequence Phe-Ile-Asp-Pro-Glu-Leu-Gln-Arg-Ser-Trp-Glu-Glu-Lys-Glu-Gly-Glu-Gly-Val-Leu-Met-Pro-Glu (SEQ ID NO:1).

8. The method of claim 6, wherein said CRIF peptide comprises the sequence Phe-Ile-Asp-Pro-Glu-Leu-Gln-Arg-Ser-Trp-Glu-Glu-Thr-Glu-Gly-Glu-Glu-Gly-Gly-Leu-Met-Pro-Glu (SEQ ID NO:2).

9. The method of claim 6, wherein said CRIF peptide comprises the sequence Glu-Gly-Glu-Gly-Val-Leu-Met-Pro-Glu (SEQ ID NO:3).

10. The method of claim 6, wherein said CRIF peptide comprises the sequence Leu-Met-Pro-Glu (SEQ ID NO:4).

11. The method of claim 1, wherein said compound is in a therapeutically effective amount.

12. The method of claim 1, wherein said compound is in a pharmaceutically acceptable carrier.

13. The method of claim 1, wherein said animal is a human.

14. The method of claim 1, wherein said compound is administered to said animal by a route of administration selected from the group consisting of oral, parenteral, intranasal, and central.

15. The method of claim 1, wherein said depressive disorder is selected from the group consisting of major depression, minor depression, bipolar disorders, disthymia, cyclothymia, and premenstrual syndrome.

* * * * *